United States Patent
Ismailova et al.

(10) Patent No.: US 11,788,408 B2
(45) Date of Patent: Oct. 17, 2023

(54) METHOD FOR DETERMINING PROPERTIES OF A FORMATION

(71) Applicant: SAUDI ARABIAN OIL COMPANY, Dhahran (SA)

(72) Inventors: Leyla Ismailova, Moscow (RU); Mokhles M. Mezghani, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 74 days.

(21) Appl. No.: 17/538,735

(22) Filed: Nov. 30, 2021

(65) Prior Publication Data

US 2023/0167738 A1 Jun. 1, 2023

(51) Int. Cl.
*E21B 49/00* (2006.01)
*G01N 33/24* (2006.01)
*E21B 21/06* (2006.01)

(52) U.S. Cl.
CPC .......... *E21B 49/005* (2013.01); *E21B 21/066* (2013.01); *G01N 33/241* (2013.01); *E21B 2200/22* (2020.05)

(58) Field of Classification Search
CPC .. E21B 21/066; E21B 49/005; E21B 2200/22; G01N 33/241
See application file for complete search history.

(56) References Cited

U.S. PATENT DOCUMENTS

| | | | |
|---|---|---|---|
| 8,101,907 B2 | 1/2012 | Jacobi et al. | |
| 10,927,671 B1 | 2/2021 | Tonner et al. | |
| 11,066,917 B2 | 7/2021 | Jain et al. | |
| 11,443,149 B2* | 9/2022 | Francois | E21B 21/06 |
| 11,492,901 B2* | 11/2022 | ElGamal | E21B 21/01 |

(Continued)

FOREIGN PATENT DOCUMENTS

| | | |
|---|---|---|
| AU | 2016206540 B2 | 2/2019 |
| CA | 2638405 A1 | 12/2009 |

(Continued)

OTHER PUBLICATIONS

Sherbeny et al. "Sinigificance of Advanced Cuttings Evaluation (ACE) Technologies for Chemostratigraphy Purposes While Drilling; Technology Overview & Applications." Society of Petroleum Engineers SPE-175860-MS (Year: 2015).*

(Continued)

*Primary Examiner* — John Fitzgerald
(74) *Attorney, Agent, or Firm* — Osha Bergman Watanabe & Burton LLP

(57) ABSTRACT

A method for determining a property of a formation, including the steps: drilling a well in the formation, collecting drill cuttings from the well, taking a digital image of each drill cutting, entering each digital image to a trained first model that outputs a predicted lithology class of each drill cutting from each digital image, taking a random number of X-ray diffraction (XRD) images of the drill cuttings, while at least one XRD image is selected from each lithology class, entering each XRD image and the corresponding digital image into a trained second model that predicts a property of the drill cuttings, and determining the property of the formation by determining the properties of the drill cuttings as a function of the depth of the drill cuttings.

20 Claims, 6 Drawing Sheets

(56) References Cited

U.S. PATENT DOCUMENTS

| | | | |
|---|---|---|---|
| 2014/0020954 A1* | 1/2014 | Pelletier | G01N 21/31 356/402 |
| 2019/0368336 A1 | 12/2019 | Hammond | |
| 2020/0157929 A1* | 5/2020 | Torrione | E21B 21/065 |
| 2020/0340907 A1* | 10/2020 | Allo | G06T 7/001 |
| 2020/0356822 A1* | 11/2020 | Starostin | E21B 49/005 |
| 2021/0019875 A1* | 1/2021 | Parmeshwar | H04N 23/90 |
| 2021/0319257 A1* | 10/2021 | Francois | G06V 10/774 |
| 2022/0179121 A1* | 6/2022 | Craddock | E21B 49/005 |
| 2023/0105670 A1* | 4/2023 | Yao | E21B 49/005 250/254 |

FOREIGN PATENT DOCUMENTS

| | | |
|---|---|---|
| CN | 109725013B B | 7/2021 |
| WO | 1994023180 A1 | 10/1994 |
| WO | 2010000055 A1 | 1/2010 |
| WO | 2020185716 A1 | 9/2020 |

OTHER PUBLICATIONS

Kathrada et al. "Visual Recognition of Drill Cuttings Lithologies Using Convolutional Neural Networks to Aid Reservoir Characterization." Society of Petroleum Engineers SPE-196678-MS (Year: 2019).*

Permata et al. "High Resolution Cuttings Analysis for Well Placement in the Uinta Basin" Unconventional Resources Technology Conference URTeC: 3118 (Year: 2020).*

Toktarov et al. "Hydrocarbon Index Identification in Lateral Section of Horizontal Wells Using Machine Learning" SPE=201382-MS (Year: 2020).*

* cited by examiner

METHOD FOR DETERMINING PROPERTIES OF A FORMATION

BACKGROUND

A geological subsurface rock formation comprises hydrocarbons in form of oil and gas. To access the hydrocarbons, a wellbore is drilled on the surface of the formation using a drill bit. During the drilling, pieces of rocks (drill cuttings) are brought to the surface. The drill cuttings provide almost immediately information about the physical and chemical properties of the formation. Sometimes the drill cuttings are the only source of information about the formation. Hence, the information about the formation needs to be as accurate and comprehensive as possible to make decisions during the drilling and afterwards.

During the collection of the drill cuttings, accidents happen where the drill cuttings at some depth intervals are not collectable. The analysis of the formation that is currently being drilled compromises collecting and analyzing non-representative drill cuttings. In some situations, drill cuttings are not representative of the current position of the drill bit. Correct determination of depth of the wellbore is crucial to accurately reference the properties of the formation.

A lab analysis for every drill cutting to obtain the properties of the formation is time consuming. Accordingly, there exists a need for a method for determining properties of a formation accurately, comprehensively, and quickly.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

One aspect of the claimed subject matter is directed to a method for determining a property of a formation, comprising the steps: drilling a well in the formation, collecting drill cuttings from the well, taking a digital image of each drill cutting, entering each digital image to a trained first model that outputs a predicted lithology class of each drill cutting from each digital image, taking a random number of X-ray diffraction (XRD) images of the drill cuttings, wherein at least one XRD image is selected from each lithology class, entering each XRD image and the corresponding digital image into a trained second model that predicts a property of the drill cuttings, and determining the property of the formation by determining the properties of the drill cuttings as a function of the depth of the drill cuttings.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments disclosed herein relate to a workflow to optimize X-ray diffraction (XRD) data acquisition from drill cutting samples to improve the mineralogy percentage prediction using Artificial Intelligence (AI). The workflow disclosed herein allows a higher prediction results accuracy using artificial intelligence with the strict necessary XRD data for the training phase.

In one aspect, embodiments disclosed herein relate to a method for determining a property of a formation, comprising the steps: drilling a well in the formation, collecting drill cuttings from the well, taking a digital image of each drill cutting, entering each digital image to a trained first model that outputs a predicted lithology class of each drill cutting from each digital image, taking a random number of X-ray diffraction (XRD) images of the drill cuttings, wherein at least one XRD image is selected from each lithology class, entering each XRD image and the corresponding digital image into a trained second model that predicts a property of the drill cuttings, and determining the property of the formation by determining the properties of the drill cuttings as a function of the depth of the drill cuttings.

Embodiments of the present disclosure may provide at least one of the following advantages. While the digital images of all the drill cuttings are taken, XRD images are only taken from a random number of the drill cuttings to determine the properties using XRD. The trained second ML model predicts the properties of the drill cuttings that were not used for XRD. This saves time and resources.

Furthermore, the method for determining properties of a formation provides an accurate determination of the mineral composition by predicting the properties of drill cuttings without physically measuring them.

Figure 1:
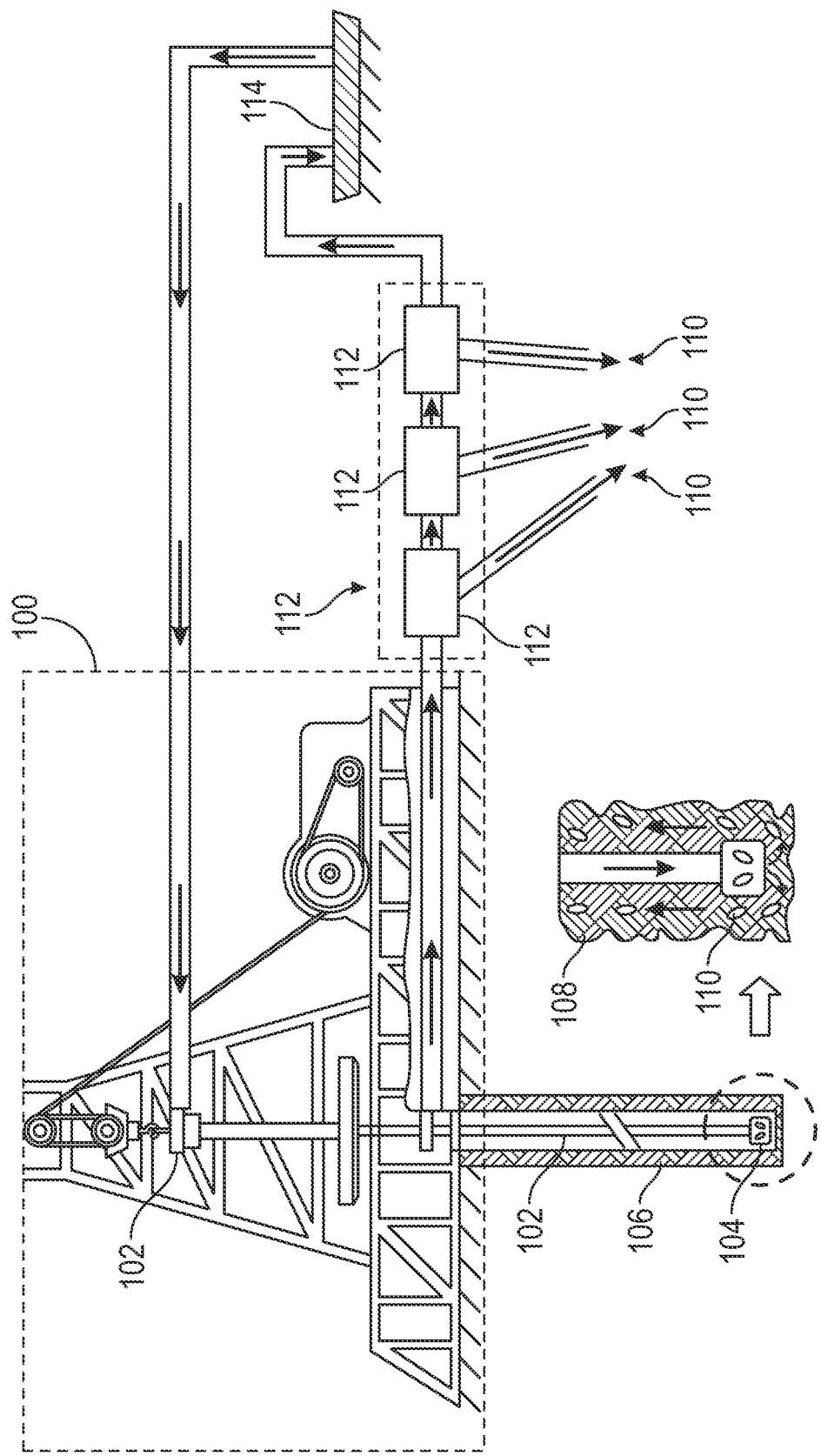
FIG. 1 shows a drilling rig, according to one or more embodiments.

FIG. 1 shows a drilling rig 100, according to one or more embodiments. The drilling rig 100 is disposed on the surface of a reservoir 106 and comprises a drill string 102 with a drill bit 104 to drill a wellbore into the formation 106. Drilling fluid 108 (drilling mud) is used to lubricate and cool the drill bit 104 while drilling the wellbore. The drilling mud 108 carries drill cuttings 110 out of the wellbore to shale shaker 112 that remove the drill cuttings 110 from the drilling mud 108. When the drill cuttings 110 are brought to the surface, they are accumulated on the shale shaker along 112 with the drilling mud 108. The drilling mud 108 is collected in a mud pit 114.

Figure 2:
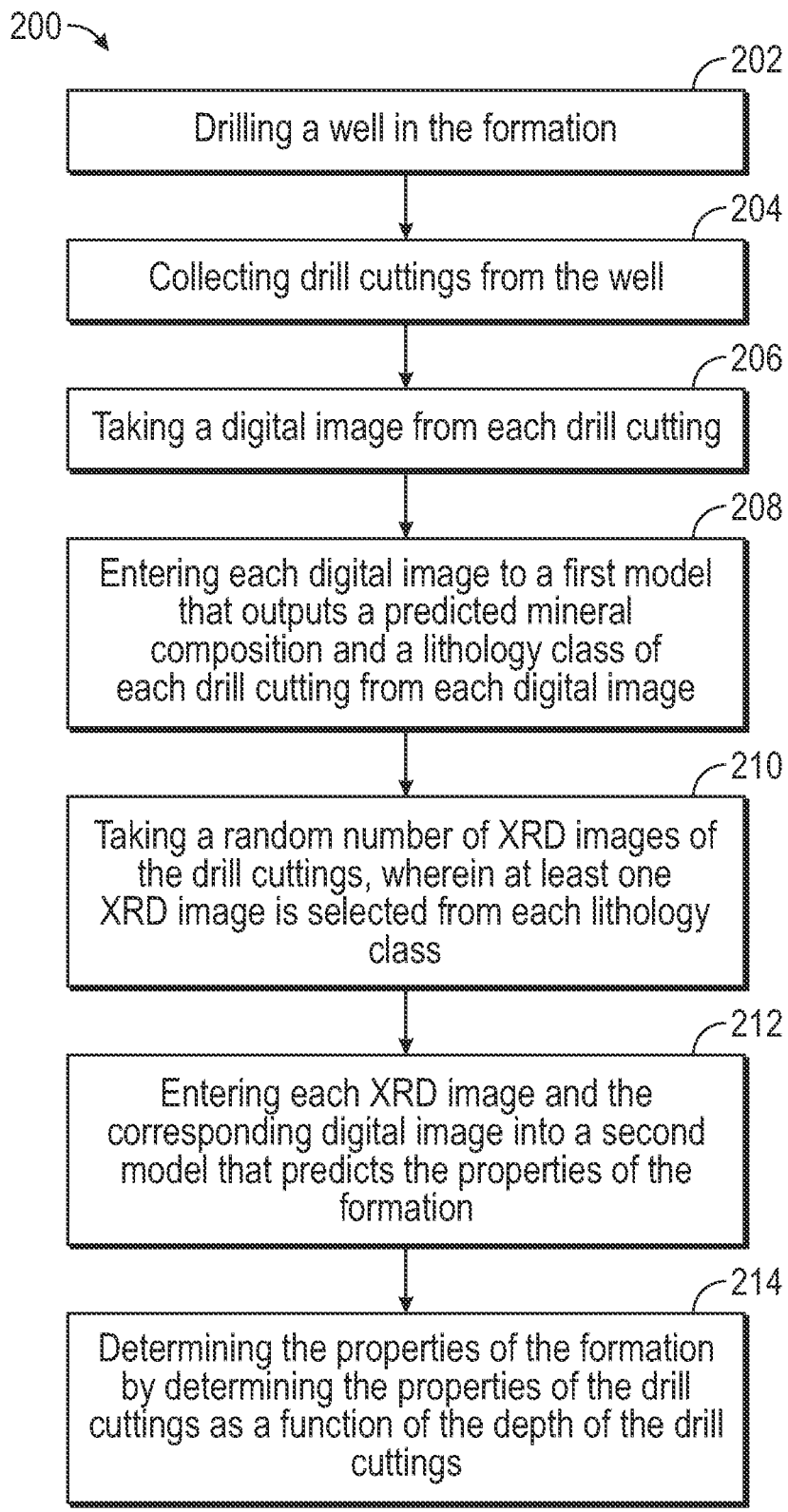
FIG. 2 shows a flowchart of the method steps for determining properties of a formation, according to one or more embodiments.

FIG. 2 shows a flowchart 200 of the method steps for determining properties of a formation.

In step 202, a wellbore is drilled in the formation using a drill bit (104 in FIG. 1).

In step 204, the drill cuttings 110 from the wellbore are collected. The drill cuttings are separated from the mud in the shale shaker. In one or more embodiments, the drill cuttings are collected from certain depth intervals of the wellbore, e. g. every 3 meter (10 feet).

In step 206, a digital image is taken from each drill cutting using any suitable image capture device, such as a camera. In one or more embodiments, the digital image comprises a high-resolution image comprising at least 300 pixel per inch (ppi). In one or more embodiments, the digital image has a format of gif, jpeg, tiff, png, eps, or raw.

In step 208, each digital image is entered to a trained first model that outputs a lithology class of each drill cutting from each digital image.

For the training of the first model, a machine learning (ML) algorithm is used to learn from and make predictions on the digital images. The ML algorithm makes predictions by entering the digital images in a mathematical ML model. The digital images used for the model are divided in multiple datasets. Three datasets are used in different stages of the training of the ML model: training, validation, and test datasets.

The ML model is initially trained on a training dataset, which is a dataset used to fit ML parameters of the ML model. The ML model is trained on the training dataset using a supervised learning method. The training dataset consists of digital images of test drill cuttings and the corresponding formation properties that are already known from the test drill cutting. The ML model is run with the training dataset and produces actual formation properties, which are then compared with test formation properties. Based on the results of the comparison and the ML algorithm being used, the ML parameters of the model are adjusted.

A supervised ML learning algorithm looks at the training dataset to learn and the optimal combinations of variables that will generate a good predictive ML model. The trained model is evaluated using new examples from the datasets to estimate the accuracy of the ML model in predicting the formation properties.

In step 210, a random number of X-ray diffraction (XRD) images are taken of the drill cuttings. At least one XRD image is taken from each lithology class. In one or more embodiments, the XRD images are calibrated to industry standards. The industry standards are the following: 1. Known mineral compositions. Diffraction peaks of the known mineral compositions are the same on each diffractometer. 2. Some of the mineral compositions comprise trace elements, however the mineral compositions with trace elements are neglected to obtain mineral compositions that are widely accepted for the formation.

X-ray crystallography or X-ray diffraction (XRD) determines the crystalline structure of the drill cuttings. A beam of incident X-rays diffracts on the crystalline structure of the drill cuttings into different directions. From the measured angles and intensities of these diffracted beams, a three-dimensional picture of the density of electrons within the drill cuttings is produced. Mean positions, chemical bonds, and crystallographic disorder of the atoms in the drill cuttings is determined from the density of the electrons.

A diffractometer is used for the XRD. The diffractometer comprises a radiation source, a monochromator that determines the wavelength of the X-rays, a detector, and a goniometer that measures an angle of the incident and diffracted beams.

For XRD a drill cutting is positioned at a certain orientations on the goniometer that measures angles of the incident and reflected beams. The drill cutting is illuminated with a finely focused monochromatic X-ray beam. The reflected beams produce a diffraction pattern of regularly spaced spots. Two-dimensional XRD images taken at different orientations are converted into a three-dimensional model of the density of electrons within the drill cutting using mathematical methods (e. g., Fourier transformation). For the XRD, the scattering of the X-rays on the drill cuttings is elastic, because the scattered X-rays have the same wavelength as the incident X-rays. Furthermore, XRD determines the mineral composition of the drill cuttings.

In one or more embodiments, performing XRD comprises selecting a drill cutting, grinding it into powder pellets, acquiring diffraction measurements, interpreting diffraction peaks, and calculating the percentage of a minerals composition from the diffraction patterns on the XRD image. The diffractometer analyzes the structure of the drill cuttings from scattering patterns produced when X-rays fall on a surface of a the drill cutting.

While the digital images of all the drill cuttings are taken, only a limited number of XRD images of the drill cuttings are analyzed by XRD. To save time and resources, the XRD analysis obtains the mineral composition of some of the drill cuttings. The method for determining properties of a formation reduces time and cost for evaluating the mineral composition of the drill cuttings.

In step 212, each XRD image and the corresponding digital image is entered in a trained second model that predicts the properties of the drill cuttings. The physical and chemical properties of the formation comprise mineral composition, grain size, porosity, and rock type. The second model is trained similarly to the first model.

In one or more embodiments, the second model comprises an artificial intelligence (AI) model that optimizes the data acquisition of the XRD of the drill cuttings and improves the prediction of the fraction of mineralogy. The ML model learns and predicts based on the properties of the drill cuttings on a historic dataset, while AI uses an intelligent agent that uses real-time data to take changes in the pattern of the digital images into account which maximizes accuracy of the trained second model. The intelligent agent perceives the environment and takes autonomous actions in order to train the second model. AI is used to predict the mineral composition of the drill cuttings from their XRD images. The accuracy of the results of the AI prediction depends on the XRD dataset used during the training. The more training data, the better the accuracy of the predictions. The method for determining properties of a formation optimizes the acquisition of XRD data and allows a higher accuracy of the prediction results using AI with the strict necessary XRD data for the training phase.

In one or embodiments, the second model comprises a deep learning model. Deep learning is a ML algorithm that uses multiple layers to progressively extract higher-level features from the input of raw digital images. In processing the digital images, lower layers identify edges of the digital images, while higher layers identify the structure of the digital images.

The deep learning model comprises an image recognition application. A digital images comprises a matrix of pixels, wherein the matrix of pixels is entered into the image recognition application as a matrix of numbers representing the matrix of pixels. A first layer of the image recognition application processes the matrix of numbers and encodes the edges of the digital images. A second layer composes and encodes arrangements of the edges. A third layer encodes the contour of the dill cuttings and a fourth layer recognizes the structure on the surface of the drill cuttings. The deep learning model learns on its own, which features need to be placed in which layer. In one or more embodiments, the placement of the features on the layers is done by hand-tuning. For example, the numbers of layers, layer sizes that provide different degrees of abstraction are tuned by hand.

The deep learning model comprises a deep neural network (DNN). The DNN is an artificial neural network with multiple layers between the input and output layers. The DNN comprises neurons, synapses, weights, biases, and functions which are trained like the ML algorithm.

In step 214, a property of the formation are determined by determining the properties of the drill cuttings as a function of the depth of the drill cuttings. In one or more embodiments, the drill cuttings are collected at every 3 meter (10 feet) of the wellbore. The properties of the drill cuttings every 3 meter (10 feet) of the wellbore indicates a property of the formation.

Figure 3:
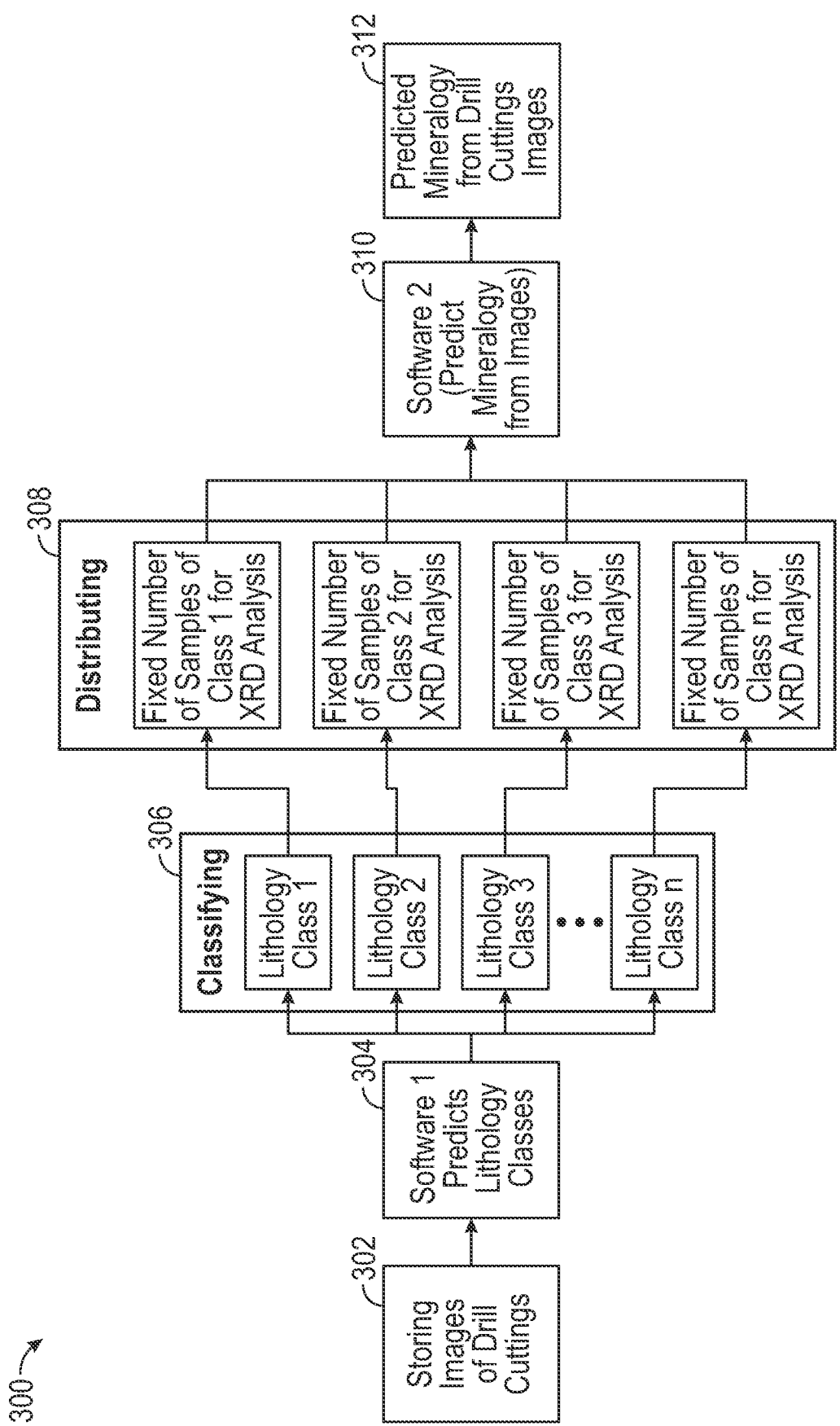
FIG. 3 shows a flow diagram of the method steps for determining properties of a formation, according to FIG. 3.

FIG. 3 shows another flowchart 300 of the method steps for determining properties of a formation, according to FIG. 2.

In step 302, the digital images taken from each drill cutting are stored. Then, the digital images are uploaded to a first software comprising the first model.

In step 304, the first software predicts the lithology classes of the drill cuttings from the digital images. As a result of the first model, various lithology classes are identified. In one or more embodiments, the lithology classes comprise carbonates, sandstones, shale, sulfates, chlorides, and igneous rocks.

In step 306, the lithology classes of the drill cuttings are stored as lithology class 1, lithology class 2, . . . , lithology class n. Next, a random number of XRD images are taken of the drill cuttings. At least one XRD image is taken in each lithology class.

In step 308, a fixed number of the XRD images are stored in their respective lithology class. For example, a fixed number of XRD images in lithology class 1 are stored, a fixed number of XRD images in lithology class 2 are stored, etc. The stored XRD images are then inputted to the second software that comprises the second model.

After the XRD images of the drill cuttings are obtained, the XRD images are uploaded to a second software comprising a second model, along with the digital images of the drill cuttings. The second model is trained based on a large dataset comprising drill cuttings of various mineralogical compositions to predict mineralogy compositions from digital images of drill cuttings. The second model utilizes ML and deep learning algorithms.

In step 310, the second model predicts mineralogy for each digital image using only a limited amount of XRD measurements. When new digital images of drill cuttings from the same well or same formation are uploaded to the second model, each mineral composition of the drill cuttings is predicted. Thus, time-consuming XRD is avoided.

In step 312, the properties of the drill cuttings from the XRD images are outputted by the second model of the second software.

Figure 4:
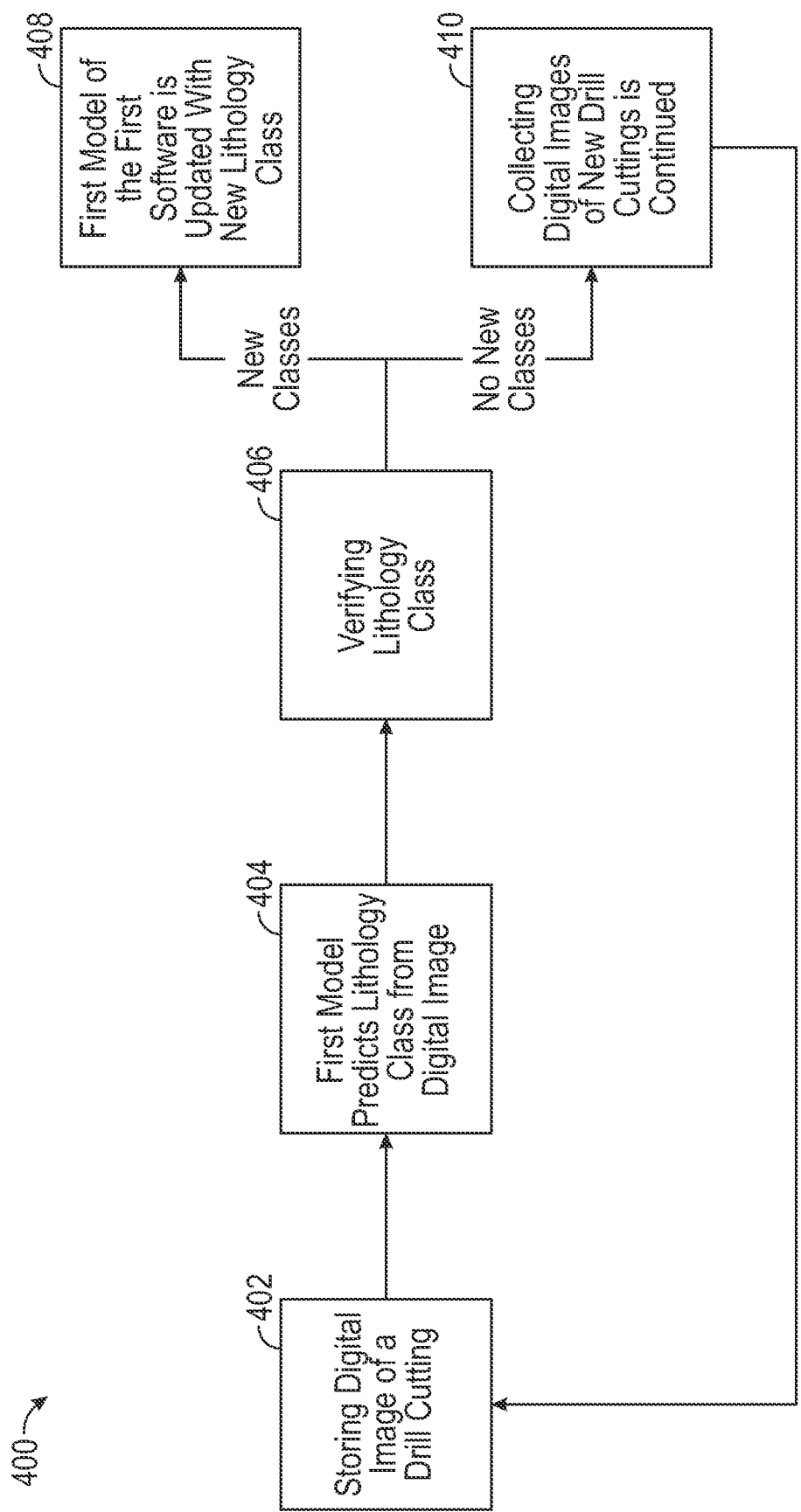
FIG. 4 shows a flow diagram of a procedure to verify the first model, according to one or more embodiments.

FIG. 4 shows a flowchart 400 of a procedure to verify the first model. In addition to the described flowchart of FIG. 2, the method for determining properties of a formation constantly verifies the first model, according to one or more embodiments. The flowchart 400 for the steps of continuously verifying the first model is illustrated in FIG. 4.

In step 402, a most recently taken digital image of a drill cutting is entered into the trained first model. This step is done by uploading the new digital image to the first software.

In step 404, the lithology class of the most recent drill cutting is predicted by the first model.

In step 406, the lithology class of the most recent drill cutting is verified. The Lithology classes are verified by inspecting minerals of the drill cutting. The minerals are identified from the mineral composition of the drill cutting. Certain minerals correspond to certain lithology classes.

In case a new lithology class is predicted by the first model, the first model is updated by adding the new lithology class "lithology class n+1" to the lithology classes lithology class 1, lithology class 2, . . . , lithology class n (see step 306 in FIG. 3).

In case no new lithology class is predicted, the algorithm of the first software continues with mineralogical composition prediction of the most recent drill cutting by XRD.

Figure 5:
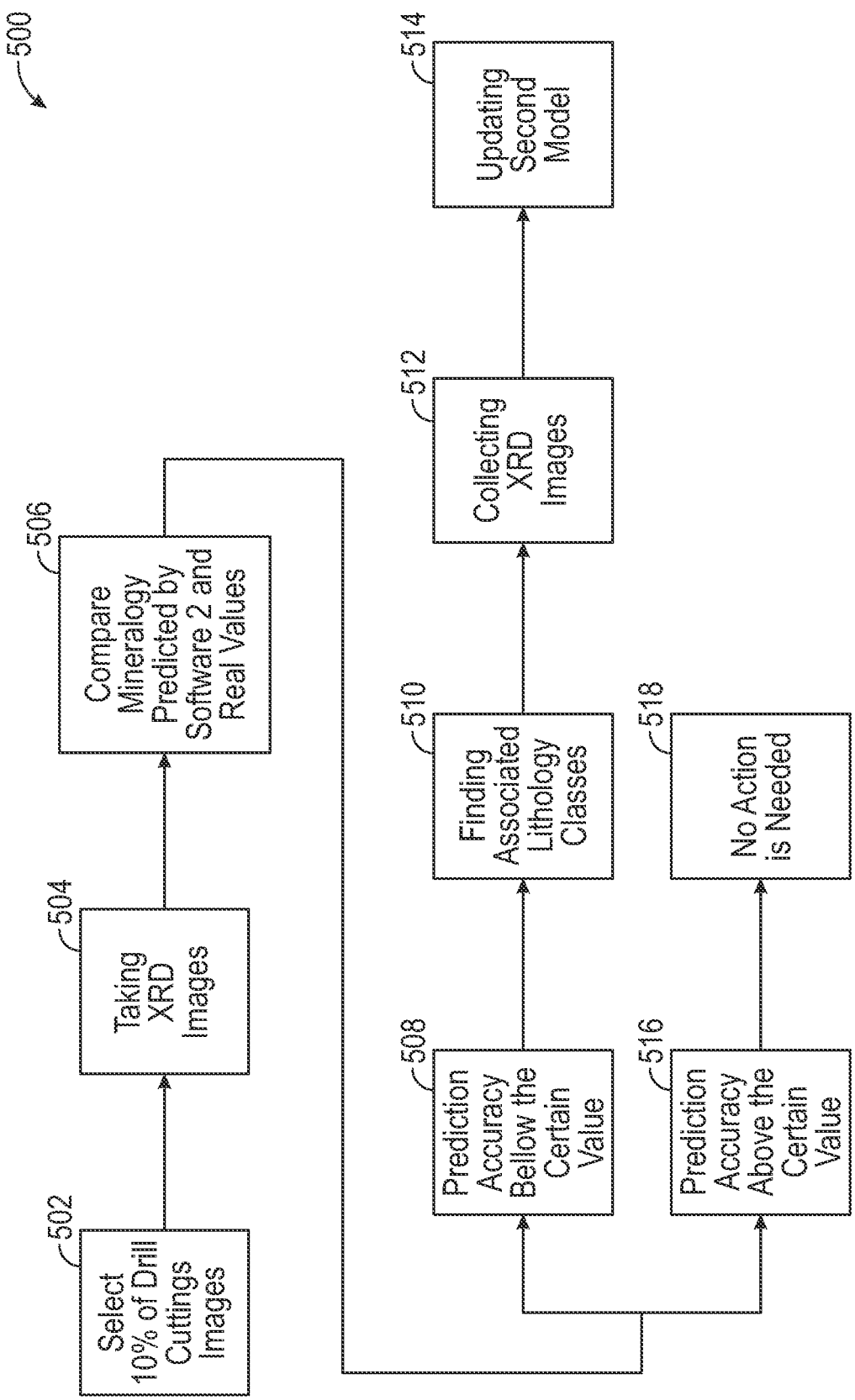
FIG. 5 shows a flow diagram of a procedure to verify the second model, according to one or more embodiments.

FIG. 5 shows a flowchart 500 of a procedure to verify the second model. In addition to the described flowchart of FIG. 2, the method for determining properties of a formation constantly verifies the second model, according to one or more embodiments. The flowchart 500 for continuously verifying the second model is illustrated in FIG. 5.

In step 502, 10% of the XRD images of the drill cuttings are randomly and periodically selected, according to one or more embodiments. In other embodiments, a random number other than 10% of the XRD images of the drill cuttings are randomly and periodically selected. At least one XRD image is selected from each lithology class.

In step 504, the diffraction is determined from the XRD images of the drill cuttings in each selected lithology classes. Once the diffraction is determined from the XRD images, the second software predicts the properties of the drill cuttings by the second model using ML. The properties of the drill cuttings along the depth the drill cuttings were obtained represent a property of the formation.

In step 506, the actual properties of the drill cuttings are compared to the predicted properties by the second model. There are two possibilities at this point. First possibility is that the accuracy of the prediction is below a certain value and the second possibility is that the accuracy of the prediction is above a certain value.

In step 508, the accuracy of the prediction is below the certain value, which leads to step 510. In step 510, the second model determines the lithology classes associated with the digital images. In step 512, XRD images are taken from a random number of drill cuttings within a certain lithology class. In step 514, the second model is updated with the new lithology class.

In step 516, the accuracy of the prediction is above a certain value, which leads to step 518. In step 518, no action is required by the user.

Figure 6:
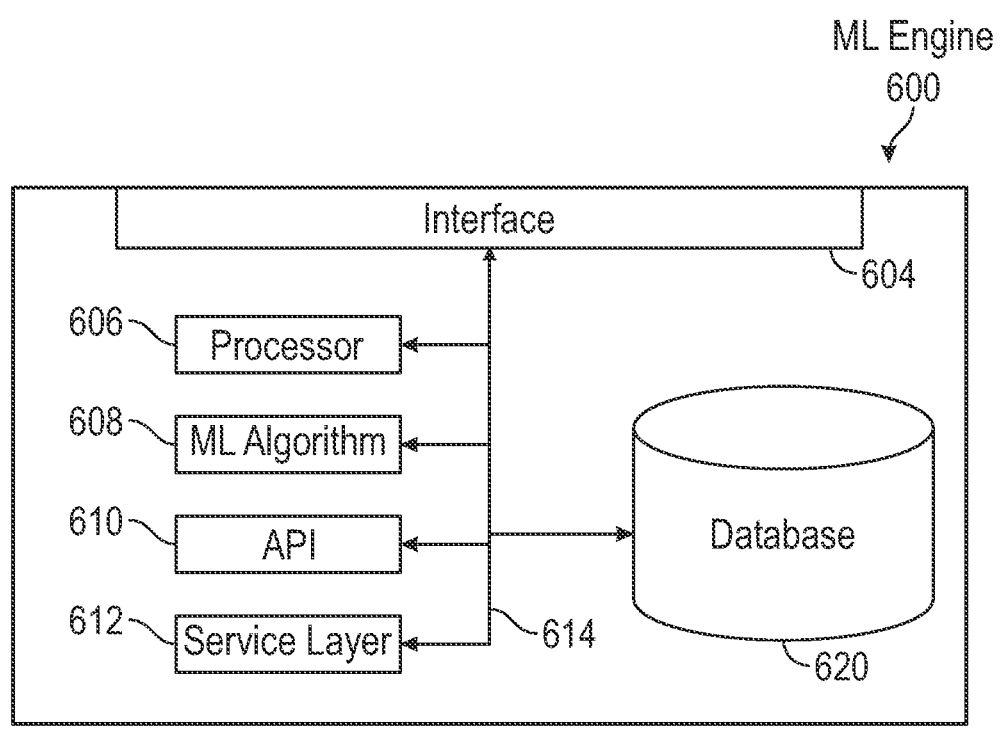
FIG. 6 shows a computer system in accordance with one or more embodiments.

FIG. 6 illustrates the ML engine 600 for the method for determining properties of a formation. In one or more embodiments, the ML engine 600 is a high performance computing (HPC) device, server, desktop computer, laptop/ notebook computer, wireless data port, smart phone, personal data assistant (PDA), tablet computing device, one or more computer processors within these devices, or any other suitable processing device, comprising both physical or virtual instances (or both) of the computing device. Additionally, the ML engine 600 comprises a computer that comprises an input device, such as a keypad, keyboard, touch screen, or other device that can accept user information, and an output device that conveys information associated with the operation of the ML engine 600, comprising digital data, visual, or audio information (or a combination of information), or a GUI.

The ML engine 600 also comprises an interface 604. The interface 604 comprises software supporting one or more communication protocols. The interface 604 further comprises hardware that receives physical signals within and outside of the illustrated ML engine 600.

The interface 604 receives the digital images and/or the XRD images from a digital camera and/or the detector of the diffractometer respectively. In one or more embodiments, the interface 604 is wirelessly connected to the digital camera and/or the detector of the diffractometer. In other embodiments, the interface 604 comprises a wired connection to the digital camera and/or the detector of the diffractometer.

Furthermore, the ML engine 600 comprises one or more ML algorithms 608 for performing the method steps for determining properties of a formation. The ML algorithm 608 is a software component of the ML engine 600. Although illustrated as an internal part of the ML engine 600, in alternative embodiments, the ML algorithm 608 is an external component of the ML engine 600.

The ML engine 600 comprises a processor 606. The processor 606 executes instructions according to the ML algorithm 608 and manipulates the digital and XRD images received from the digital images and/or the detector of the diffractometer to perform the method steps for determining a property of the formation according to the ML algorithm 608.

The ML engine 600 further comprises a database 620. The existing digital and/or XRD images are stored in the database 620. While the database 620 is illustrated as an integral component of the ML engine 600, in alternative embodiments, the database 620 is external to the ML engine 600. The database 620 may be any repository capable of storing data, including but not limited to data structures such as tables, lists, arrays, etc.

The interface 604, the processor 606, the ML algorithm 608, and the database 620 communicate via a system bus 614. In one or more embodiments, any or all of the interface 604, the processor 606, the ML algorithm 608, and the database 620, communicate with each other over the system bus 614 using an application programming interface (API) 610 or a service layer 612 or a combination of the API 610 and service layer 612.

In one or more embodiments, the ML algorithm 608 creates a ML model with an artificial neural network (ANN). The ANN comprises neurons, wherein each neuron is connected to every other neuron in the ANN. A neuron receives data then processes it and sends the data to all the other neurons. The neurons are aggregated and organized into layers. The neurons of a layer are connected to all the neurons of the neighboring layers. A first layer is the input layer that receives the existing data logs. The last layer is the output layer that outputs the estimated pore pressure log. The mineral composition of the formation is predicted from the digital images of the drill cuttings using ANN.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method for determining a property of a formation, comprising the steps:
   drilling a well in the formation,
   collecting drill cuttings from the well,
   taking a digital image of each drill cutting,
   entering each digital image to a trained first model that outputs a predicted lithology class of each drill cutting from each digital image,
   taking a random number of X-ray diffraction (XRD) images of the drill cuttings, wherein at least one XRD image is selected from each predicted lithology class,
   entering each XRD image and the corresponding digital image into a trained second model that predicts a property of the drill cuttings, and
   determining the property of the formation by determining the properties of the drill cuttings as a function of the depth of the drill cuttings.

2. The method of claim 1, wherein the property of the formation comprises mineral composition, grain size, porosity, and rock type.

3. The method of claim 1, wherein the first model is verified by constant monitoring of the predicted lithology classes.

4. The method of claim 1, wherein the second model is verified by periodically monitoring the properties of the drill cuttings.

5. The method of claim 1, wherein the properties of the drill cuttings are monitored by comparing the predicted class with the actual class of the properties of the drill cuttings.

6. The method of claim 1, wherein the first model comprises an artificial intelligence (AI) model.

7. The method of claim 1, wherein the first model comprises a machine learning model.

8. The method of claim 1, wherein the first model comprises a deep learning model.

9. The method of claim 1, wherein the second model comprises an artificial intelligence (AI) model.

10. The method of claim 1, wherein the second model comprises a machine learning model.

11. The method of claim 1, wherein the second model comprises a deep learning model.

12. The method of claim 1, wherein the XRD images are calibrated to industry standard.

13. The method of claim 1, wherein the digital images are in the following data format: gif, jpeg, tiff, png, eps, or raw.

14. The method of claim 1, wherein the XRD images are in the following data format: gif, jpeg, tiff, png, eps, or raw.

15. The method of claim 1, wherein the first model is embedded in a first software.

16. The method of claim 1, wherein the second model is embedded in a second software.

17. The method of claim 1, wherein the first and second model are embedded in a single software.

18. The method of claim 1, wherein the drill cuttings are collected at every 3 meter (10 feet) of the wellbore.

19. The method of claim 1, wherein digital images of drill cuttings with low accuracy of the predicted lithology class are used to create a new lithology class.

20. The method of claim 1, wherein the digital images comprise high-resolution images with at least 300 ppi.

\* \* \* \* \*